(12) United States Patent
Savio et al.

(10) Patent No.: US 8,007,776 B2
(45) Date of Patent: Aug. 30, 2011

(54) VACCINE COMPOSITION COMPRISING INTERLEUKIN-15 (IL-15)

(75) Inventors: Alicia Santos Savio, Ciudad de la Habana (CU); Ricardo Silva Rodriguez, Ciudad de la Habana (CU); Yanelis Morera Diaz, Ciudad de la Habana (CU); Armando Alexei Rodriquez Alfonso, Ciudada de la Habana (CU); Jose Rafael Martinez Castillo, Ciudad de la Habana (CU); Haydee Geronimo Perez, Ciudad de la Habana (CU); Alejandro Moro Soria, Ciudad de la Habana (CU); Silvio Ernesto Perea Rodriguez, Ciudad de la Habana (CU)

(73) Assignee: Centro de Ingenieria Genetica y Biotecnologia, Cuidad de la Habana (CU)

( * ) Notice: Subject to any disclaimer, the term of this patent is extended or adjusted under 35 U.S.C. 154(b) by 569 days.

(21) Appl. No.: 10/529,923

(22) PCT Filed: Oct. 8, 2003

(86) PCT No.: PCT/CU03/00010
§ 371 (c)(1),
(2), (4) Date: Aug. 29, 2005

(87) PCT Pub. No.: WO2004/032956
PCT Pub. Date: Apr. 22, 2004

(65) Prior Publication Data
US 2006/0182713 A1 Aug. 17, 2006

(30) Foreign Application Priority Data
Oct. 9, 2002 (CU) .................................. 2002/0218

(51) Int. Cl.
*A61K 38/20* (2006.01)
(52) U.S. Cl. ...................................... 424/85.2; 530/351
(58) Field of Classification Search .......................... None
See application file for complete search history.

(56) References Cited

U.S. PATENT DOCUMENTS

| 5,894,018 | A | 4/1999 | Davila et al. |
| 6,013,480 | A * | 1/2000 | Grabstein et al. ............ 435/69.1 |
| 6,344,192 | B1 * | 2/2002 | Grooten et al. ............... 424/85.2 |

FOREIGN PATENT DOCUMENTS

| WO | WO 95/27722 | * 10/1995 |
| WO | 00 02582 A | 1/2000 |

OTHER PUBLICATIONS

Gonzalez S. et al. P64k meningococcal protein as immunological carrier for wek immunogens. Scand. J. Immunol. 2000. vol. 52, p. 113-116.*
Schwartz RH and Mueller DL. Immunological Tolerance. In Fundamental Immunology, 5th Edition. 2003. W.E. Paul (Ed)., Lippincott, Williams, and Wilkins.*
Al-Mughales J, et al. The chemoattractant activity of rheumatoid synovial fluid for human lymphocytes is due to multiple cytokines. Clin. Exp. Immunol. 1996. vol. 106, pp. 230-236.*
Obermeier F, et al. IL-15 protects intestinal epithelial cells. Eur. J. Immunol. 2006. vol. 36, pp. 2691-2699.*
Kukita T, et al. Autocrine and/or paracrine growth of adult T-cell leukemia tumour cells by interleukin 15. Br. J. Haematol. 2002. vol. 119, pp. 467-474.*
Brewer JM, et al. Aluminum hydroxide adjuvant initiates strong antigen-specific Th2 responses in the absence of IL-4- or IL-13-mediated signaling. J. Immunol. 1999. vol. 163, pp. 6448-6454.*
Fehniger Todd A, et al., "Interleukin 15: biology and relevance to human disease", *Blood* 2001, 97: 14-32.

* cited by examiner

*Primary Examiner* — Marianne C Seidel
*Assistant Examiner* — Bruce D Hissong
(74) *Attorney, Agent, or Firm* — Hoffmann & Baron, LLP

(57) ABSTRACT

Vaccine composition containing IL-15 for active immunization to treatment diseases related to over-expression of this cytokine. The technical aim pursued in this invention is to inhibit IL-15 activity through development of a therapeutic vaccine which elicits IL-15 neutralizing antibodies in the immunized host.
IL-15 can be presented in this vaccine composition either alone or coupled to a carrier such as the P64k protein with a vaccine adjuvant such as Aluminum hydroxide.
Besides, this invention is related to the use of this vaccine for treatment of Rheumatoid arthritis and other IL-15 over-expressing related diseases, and leukemia, where this cytokine acts as a growth factor.

2 Claims, 2 Drawing Sheets

VACCINE COMPOSITION COMPRISING INTERLEUKIN-15 (IL-15)

This application is a U.S. National Phase Application of International Application No. PCT/CU2003/000010 filed on Oct. 8, 2003. The specification of International Application No. PCT/CU2003/000010 is hereby incorporated by reference.

This application asserts priority to Cuban Application No. CU 2002-0218 filed on Oct. 9, 2002. The specification of Cuban application No. CU 2002-0218 is hereby incorporated by reference.

This invention is related to the immunology branch, particularly to a new IL-15 use for active immunization to treatment IL-15 over-expressing related diseases.

BACKGROUND OF THE INVENTION

This cytokine known as IL-15 is a 14-15 KDa glycoprotein, which was simultaneously described by two groups as a T cells-activating growth factor (Grabstein, K. H. et al., Science 1994, 264, 965; Burton, J. D. et al., Proc. Natl. Acad. Sci. USA 1994, 91, 4935). IL-15 mRNA is widely present in cells and tissues, however, it is difficult to find the protein in these cells or in the cells supernatant due to a strong post-transcriptional control of its expression at the translational level and the intracellular traffic (Bamford R N. et al, J. Immunol 1998, 160: 4418-4426), (Kurys G, et al, J Biol Chem 2000, 275: 30653-30659).

The IL-15 biological effects are mediated through its binding to a cell membrane receptor composed of three subunits $\alpha$, $\beta$, and $\gamma$. The IL-15R$\alpha$ is a specific subunit for this cytokine to whom is bound with a very high affinity Kd $10^{-11}$, $\beta$ subunit is shared with IL-2 and $\gamma$ subunit is a common receptor for several cytokines, IL-2; Il-4; IL-7; IL-9; IL-15; IL-21 (Bamford R N., et al, Proc. Natl. Acad. Sci. USA 1994, 91, 4935), (Giri J G., et al, EMBO J. 1995, 14: 3654-3663).

The IL-15 is an immunostimulatory cytokine promoting proliferation and functional activity of T, B and NK cells (Giri, J. G., EMBO J. 1994, 13, 2822-2830), activates neutrophiles and modifies monokine secretion (Girard D., 1996, Blood, 88, 3176; Alleva D. G., 1997, J. Immunol., 159, 2941). This cytokine mediates different effects on several steps of the immune response, induces CD56 NK cells proliferation and acts, together with IL-12, inducing IFN$\gamma$ and TNF$\alpha$ (Ross M E, 1997, Blood 89, 910-918; Fehniger T A, 1999, Transplant Proc, 31, 1476-1478).

The binding of the ligand to the T cell receptor induces expression of IL-15R$\alpha$ and expression of several activation antigens such as CD69, CD25 and TNFRII. Also IL-15 is a chemoattractant for human blood T lymphocytes (Wilkinson 1995, J. Exp. Med. 181, 1255-1259). All these data suggest that IL-15 expressed by antigen presenting cells could be important on the early T cell activation at the inflammation site.

Il-15 has been detected in the course of several diseases including Crohn's disease (Kirman I., 1996, *Am. J. Gastroenterol.* 91, 1789), Psoriasis (Rückert R. 2000, 165: 2240-2250), Leukemia (Yamada Y. 1999, *Leukemia and Limphoma*, 35(1-2): 37-45) and Rheumatoid arthritis (RA), (McInnes I. B. 1998, *Immunology Today*, 19, 75-79).

Feldmann et al., 1996, *Annu Rv Immunol*, 14: 397-440) proposed TNF$\alpha$ as the main cytokine in a cytokine cascade that includes IL-1$\beta$, IL-6, GM-CSF and several inflammatory cytokines such as Mip 1$\alpha$, Mip 1$\beta$ and IL-8, which are closely related to the development and progression of the Rheumatoid arthritis (RA). McInnes et al., found IL-15 expression abnormalities in this disease, high IL-15 concentration in the synovial fluid and its expression in synovial membrane cells. They suggested that IL-15 precedes TNF$\alpha$ in the cytokine cascade, proposing a mechanism dependent on cell contact, where, IL-15 activated T cells induce TNF$\alpha$ synthesis by macrophages. Moreover, it is proposed that IL-15 acts as an important factor on the T cell migration to the synovial fluid (McInnes, 1997, *Nat Med*, 3: 189-195).

Ziolkowska et al., reported that IL-15 induces IL-17 expression at joints from RA patients, it is already known that this cytokine stimulates release by synoviocytes of several inflammatory mediators such as IL-6, IL-8, GM-CSF, and prostaglandine $E_2$ suggesting an important role for IL-15 in the RA pathogenesis (Ziolkowska y col 2000, J Immunol, 164: 2832-2838).

T cells recruitment and activation may occur as a consequence of IL-15 local synthesis and such non specific activation could bring as a result an endless inflammation. All this suggest that IL-15 inhibition could have a therapeutic potential on the disease treatment.

The use of IL-15 antagonist molecules has been shown to be effective in animal models. Ruchatz et al. generated a soluble fragment from the alpha subunit of the murine receptor (IL-15R$\alpha$) and demonstrated that this fragment inhibited collagen-induced arthritis when it was administered to DBA/1 mice (Ruchatz H. 1998, *J. Immunol.* 160: 5654-5660).

Other IL-15 antagonist molecules have been patented including IL-15 mutated in one or more amino acids residues and monoclonal antibodies capable to bind mature IL-15 and prevent signal transduction through its receptor (U.S. Pat. No. 6,001,973, U.S. Pat. No. 6,177,079, U.S. Pat. No. 6,168,783, and U.S. Pat. No. 6,013,480). Although their use is described in the above mentioned patent files, there are quite a few results published in scientific journals supporting their efficacy. On May 2002, Genmab Company revealed phase I/II clinical studies with an antibody against IL-15 patented by Immunex, which must correspond to previously referred U.S. Pat. No. 6,177,079, but these results have not been published yet.

Other studies have been done with the chimera protein MutIL15-Fc that binds to cells carrying the IL-15 receptor, which leads to a reduced number of activated immune cells below a critical level and induces tolerance, e.g., self-reactive activated T cells with a key role in allograft rejection are responsive to IL-15 and has been demonstrated that they can be inhibited by using MutIL15-Fc protein, which acts as an IL-15 antagonist.

There are a few examples on the vaccine bibliography to generate antibodies against autologous molecules, e.g., a vaccine against EGF for the treatment of EGF dependent tumors (U.S. Pat. No. 5,894,018), its efficacy has been demonstrated in clinical trials by eliciting antibodies that block EGF activity. The generation of neutralizing antibodies against autologous proteins is very complex due to natural mechanisms to tolerate your self

SUMMARY OF THE INVENTION

In the current invention, active immunization with IL-15 in a proper formulation to generate neutralizing self-antibodies against IL-15 makes possible neutralization of the anomalous quantities of this cytokine found in patients with autoimmune diseases and leukemia.

In current invention an active immunization is done allowing generation of IL-15 neutralizing self-antibodies, being IL-15 levels regulated through an immunization scheme.

DETAILED DESCRIPTION OF THE INVENTION

The essence and novelty of the current invention are in the vaccine composition using IL-15 for active immunization to treatment IL-15 over-expressing-related diseases.

This vaccine composition will be used in humans in order to elicit a neutralizing antibodies response against autologous IL-15.

This invention also includes IL-15 fused to a carrier protein as well as any other formulation comprising them.

The invention also contemplates the use of the vaccine alone or concurrently with anti-inflammatory drugs or other cytokines antagonists.

According to some embodiments of the invention, a mammalian expression vector comprises a DNA sequence coding for II-15 in a proper formulation for active immunization.

According to some embodiments of the invention, IL-15 is a recombinant protein obtained in *E. coli*, therefore, its glycosilation pattern is different from the autologous IL-15. In some embodiments of the invention, IL-15 is an active protein with a specific activity of $2-5 \times 10^6$ U/mg according to the CTLL-2 assay.

The IL-15 gene of the invention was isolated form LPS-activated monocytes and cloned into an *E. coli* expression vector and purified from this source. The protein biological activity was determined by induction of T cells proliferation on the CTLL2 assay.

According to some embodiments of this invention, fusion protein p64IL-15 was obtained by designing oligonucleotides that allow IL-15 gene amplification by PCR and insertion of this gene into an *E. coli* expression vector containing the gene coding for the p64k protein. The IL-15 protein was fused to the C-terminal region of the p64k carrier protein and purified from this source. The protein biological activity was determined by induction of T cells proliferation on the CTLL2 assay.

The proof-of-concept shown in this invention was demonstrated by using *macacus irus* monkeys as a model, their IL-15 has a 96.4% homology to human IL-15.

According to the present invention, results are provided which demonstrated that active immunization with either IL-15 or fusion protein p64kIL-15 generated both an antibody response specific for IL-15 and neutralizing antibodies on immunized animals' sera.

The object of this invention is also extensive to a DNA vaccine comprising a vector containing a DNA coding for the human IL-15 according to the present invention and its use as alternative in the gene therapy of IL-15 expression related diseases.

Described vaccine can be concurrently administered with anti-inflammatory or immunesuppressor agents or other cytokines antagonists used to treatment RA.

EXAMPLES

The following examples are provided to illustrate current invention embodiments

Example 1

Obtaining Recombinant IL-15

DNA coding for human IL-15 was isolated by RT-PCR from LPS-activated monocytes and cloned into an *E. coli* expression vector.

Figure 1:
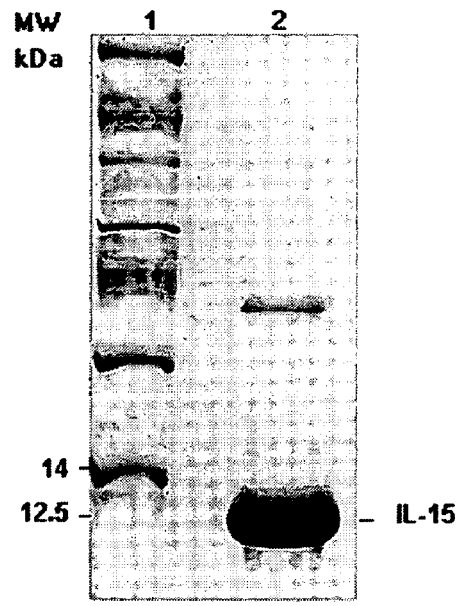
FIG. 1: Purity of IL-15

Recombinant IL-15 expressed in *E. coli* was extracted from cellular pellet with urea 8M and purified by a chromatography in TSK G4000SW (Merck) followed by a chromatography in RP-C4 (J. T. Baker) in a water/acetonitrile, TFA buffer system. Biological activity was measured by stimulation of the CTLL-2 cell line proliferation using MTT mitochondrial staining (Cosman y col 1984, Nature, 312: 768-771). 11-15 specific activity is $2 \times 10^6$ U/mg (FIG. 1).

Obtaining Recombinant p64k-IL15 Fusion Protein

Figure 2:
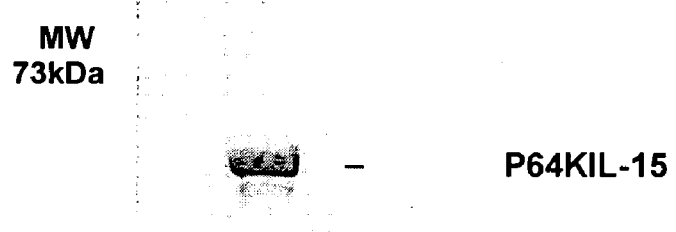
FIG. 2: Purity of fused protein

P64k-IL15 fusion protein was obtained by designing oligonucleotide primers that would amplify the IL-15 gene by PCR and insert it at the p64k c-terminus into an *E. coli* expression vector (FIG. 2).

The protein is soluble after cellular rupture in a French press.

Streptomycin sulphate is added up to 0.8% to the rupture supernatant, which is kept at 4° C. for 1 h, centrifuged 15 min at 10000 rpm, and 4° C. Two precipitation steps with ammonium sulphate are carried out and pellet is suspended in Tris 20 mM, EDTA 6 mM, Urea 2 M, pefabloc 0.5 mg/mL and purified through an ionic exchange chromatography in TSK DEAE PW and gel filtration in SUPERDEX 200.

Example 2

Evaluation Model in Monkeys *Macacus Irus*

Figure 3:
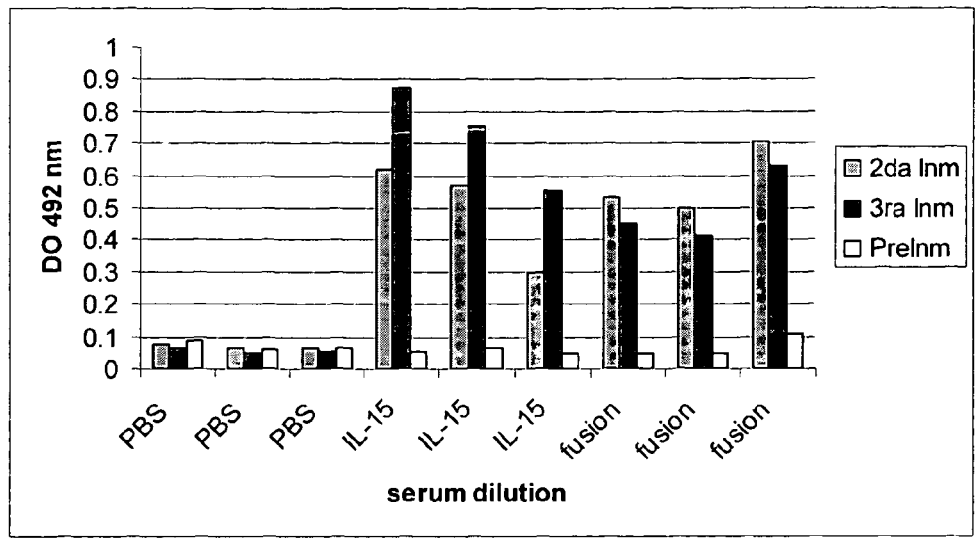
FIG. 3: Results of an ELISA test showing levels of anti-IL-15 antibodies in monkeys
Figure 4:
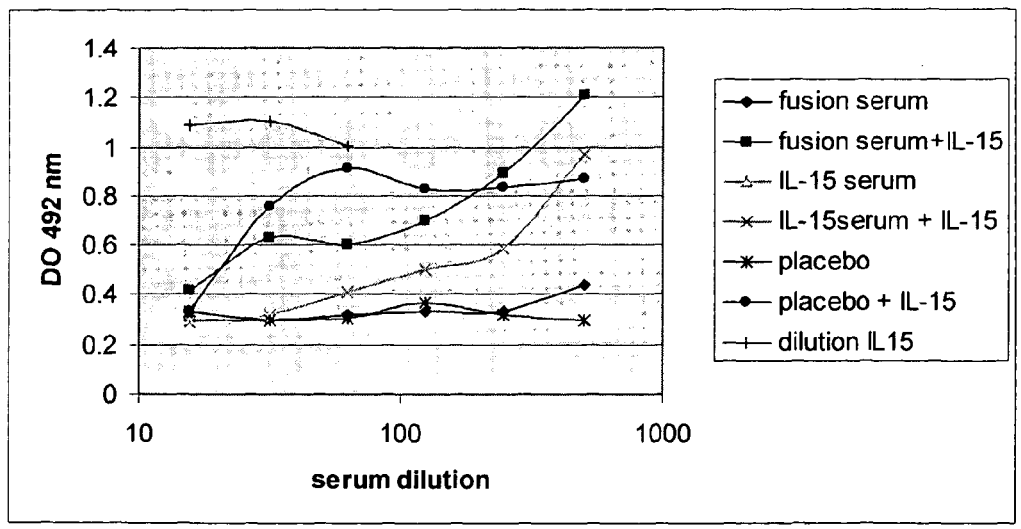
FIG. 4: Determination of IL-15 neutralizing antibodies in monkey's sera

Three groups were evaluated in a monkeys immunization scheme, immunized with IL-15; immunized with the fusion protein and placebo. The proteins were administered in amounts of 100 μg per inoculation in Freund's adjuvant. First immunization was done with Freund's complete adjuvant, second immunization with incomplete Freund's adjuvant one month later and third immunization with incomplete Freund's adjuvant was done two months later. One week after second and third immunization blood was extracted to evaluate level of anti-IL15 antibodies in the monkeys' sera. Data are shown in FIG. 3

Example 3

Determination of Neutralizing Antibodies in Monkeys' Sera

The cytokine-dependent cell line CTLL-2 proliferates in presence of IL-15. IL-15 bound molecules impairing receptor depending signal transduction would inhibit this cell line proliferation.

To evaluate the neutralizing capacity of antibodies present in monkeys' sera, serial dilutions of them were done in 96 well plates (Costar, USA) in 50 μL volume of RPMI medium (Gibco) supplemented with 10% fetal bovine serum (Gibco). A sub-optimal amount of IL-15 (30 pg) was added to each well and previously washed CTLL-2 cells were added to $5 \times 10^3$ cells/well. Plate was incubated for 48 h at 5% $CO_2$ and 37° C. To measure proliferation MTT mitochondrial staining was used (Cosman et al. 1984, Nature, 312: 768-771). In results shown in FIG. 3 it is observed that antibodies-mediated inhibition of IL-15 induced proliferation.

Invention Advantages:

Levels of generated antibodies are more stable throughout time than antibodies obtained by a passive immunization Lesser frequency of doses administration to patients compared to passive immunization Required amount of protein per dose and amount of doses are quite inferior to the required for treatment with IL-15 antagonist molecules; this implies a lower production cost.

The invention claimed is:

1. A method for generating a neutralizing antibody response against autologous IL-15 in a primate, wherein said method comprises administering to said primate a composition comprising human IL-15 and aluminum hydroxide, wherein the IL-15 is an antigen and wherein said IL-15 antigen generates neutralizing self-antibodies against IL-15.

2. The method according to claim 1, wherein the IL-15 antigen is coupled to a carrier protein, and wherein the carrier protein is P64k protein.

* * * * *